United States Patent

Ikeda et al.

[11] Patent Number: 5,565,085
[45] Date of Patent: Oct. 15, 1996

[54] METHOD FOR QUANTIFYING SPECIFIC COMPOUND

[75] Inventors: Shin Ikeda, Katano; Toshihiko Yoshioka, Osaka; Shiro Nankai, Hirakata; Haruhiro Tsutsumi, Onsen-gun; Hideyuki Baba; Yoshinobu Tokuno, both of Matsuyama, all of Japan

[73] Assignee: Matsushita Electric Industrial Co., Ltd., Kadoma, Japan

[21] Appl. No.: 428,040

[22] Filed: Apr. 25, 1995

[30] Foreign Application Priority Data

Apr. 25, 1994 [JP] Japan ................................ 6-086579
Mar. 8, 1995 [JP] Japan ................................ 7-048529

[51] Int. Cl.⁶ .......................................... G01N 27/26
[52] U.S. Cl. ................. 205/777.5; 205/778; 204/403; 204/406; 435/817; 435/287.1; 435/287.9
[58] Field of Search .......................... 204/153.12, 403, 204/406; 435/817, 288, 291

[56] References Cited

U.S. PATENT DOCUMENTS 5,266,179  11/1993  Nankai et al. ........................ 204/416
5,352,351  10/1994  White et al. ........................ 204/406

FOREIGN PATENT DOCUMENTS 00502504  9/1992  European Pat. Off. .
62156555  12/1987  Japan .

*Primary Examiner*—Bruce F. Bell
*Attorney, Agent, or Firm*—McDermott, Will & Emery

[57] ABSTRACT

A biosensor for quantifying a specific compound has a reaction layer containing at least an enzyme, and an electrode system having a working electrode and a counter electrode formed on an insulating base plate; the biosensor detects the specific compound contained in a sample on the basis of an electrochemical response. In quantifying, the working electrode and the counter electrode are short-circuited before the voltage is applied therebetween. The short-circuiting eliminates measuring errors that may occur due to nonuniform dissolution of the reaction layer in a sample, and achieves highly reliable quantification of a specific compound.

4 Claims, 5 Drawing Sheets

METHOD FOR QUANTIFYING SPECIFIC COMPOUND

BACKGROUND OF THE INVENTION

1. Field of the Invention

The present invention relates to a method for quantifying a specific compound, such as glucose, contained in a sample.

2. Description of the Prior Art

As an example of a quantifying method for a specific compound, a method of quantifying glucose will be described below.

In a generally known method of electrochemically quantifying glucose, a glucose oxidase (EC 1.1.3.4) is used in combination with an oxygen electrode or a hydrogen peroxide electrode (described, for example, in "BIOSENSOR", Kodansha, edited by Shuichi Suzuki).

The glucose oxidase selectively oxidizes β-D-glucose, the substrate, into D-glucono-δ-lactone using oxygen as an electron acceptor. In this reaction process, the oxygen is reduced to hydrogen peroxide. The quantity of the glucose can be determined by measuring an amount of oxygen consumption with an oxygen electrode or by measuring an amount of generated hydrogen peroxide with a hydrogen peroxide electrode.

According to the above method, as can be inferred from the reaction process, the results of measurement are greatly influenced by the concentration of oxygen dissolved in the sample solution. Furthermore, measurements cannot be made in the absence of oxygen.

In view of the above situation, a new type of glucose sensor has been developed that uses instead of oxygen an organic compound or a metal complex, such as a potassium ferricyanide, ferrocene derivative, quinone derivative, etc., as the electron acceptor. In this type of sensor, the reduced form of the electron acceptor, resulting from the enzymatic reaction, is oxidized with an electrode and the concentration of glucose is determined from its oxidizing current.

Furthermore, when such an electron acceptor is used in place of oxygen, a known amount of glucose oxidase and the electron acceptor can be held on the electrode accurately and in a stable condition. In that case, the electrode system and the reaction layer can be formed in an integral structure in a near dry condition. Disposable glucose sensors based on this technique have been attracting much attention in recent years, since the concentration of glucose can be easily measured just by introducing a test sample into a sensor chip inserted in a measuring device. This method can be applied to the quantification not only of glucose but also of other specific compounds.

The use of the above-mentioned electron acceptors, which is coupled with the technique for forming the electrode system and the reaction layer in an integral structure, has made possible simple electrochemical quantification of various specific compounds. However, in quantifying a specific compound using the above-mentioned method, if there is nonuniformity in the dissolved state of the reaction layer in the test sample, there may occur nonuniformity, for example, in the wetting of the working electrode and counter electrode with respect to the test sample or in the state of an electric double layer formed at the interface between the respective electrode and the substance dissolved in the sample solution, thus causing a potential difference between the two electrodes. This potential difference causes errors or variations in the results of measurement.

SUMMARY OF THE INVENTION

It is an object of the present invention to provide a method for quantifying a specific compound, which eliminates the above-mentioned deficiencies.

According to the present invention, there is provided a method for quantifying a specific compound, which uses a biosensor comprising a reaction layer containing at least an enzyme, and an electrode system having a working electrode and a counter-electrode formed on an insulating base plate, and which detects the change in substance concentration caused by the reaction between the enzyme and the specific compound contained in a sample on the basis of an electrochemical response obtained when a voltage is applied between the working electrode and the counter electrode, characterized in that the working electrode and the counter electrode are short-circuited before the voltage is applied therebetween.

According to the present invention, there is also provided a quantifying method wherein the circuit between the working electrode and the counter electrode is alternately closed and opened a plurality of times before applying voltage between the working electrode and the counter electrode.

The present invention provides an apparatus for quantifying a specific compound, comprising: a biosensor including a reaction layer containing at least an enzyme, and an electrode system having a working electrode and a counter electrode formed on an insulating base plate; means for supplying a sample solution containing a specific compound to the reaction layer of the biosensor; voltage application means for applying a predetermined voltage between the working electrode and the counter electrode of the biosensor; means for measuring a current flowing between the working electrode and the counter electrode to which the voltage is applied; means for short-circuiting the working electrode and the counter electrode before the voltage is applied between the working electrode and the counter electrode.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE PREFERRED EMBODIMENTS

First, we will describe the structure of a glucose sensor as an example of the biosensor used in the quantifying method of the present invention.

Figure 1:
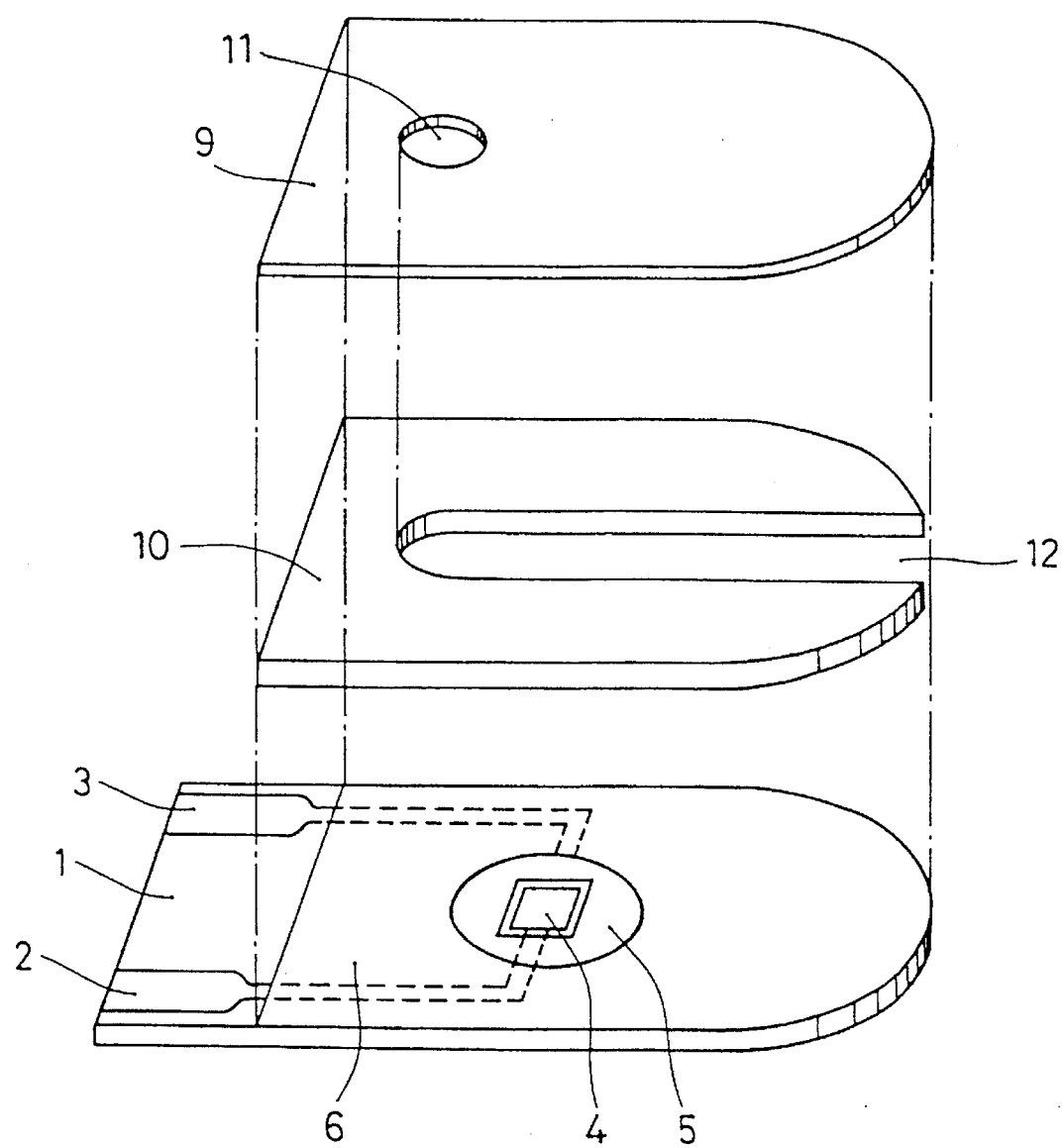
FIG. 1 is an exploded view, with a reaction layer omitted, of a glucose sensor used in one example of the present invention.
Figure 2:
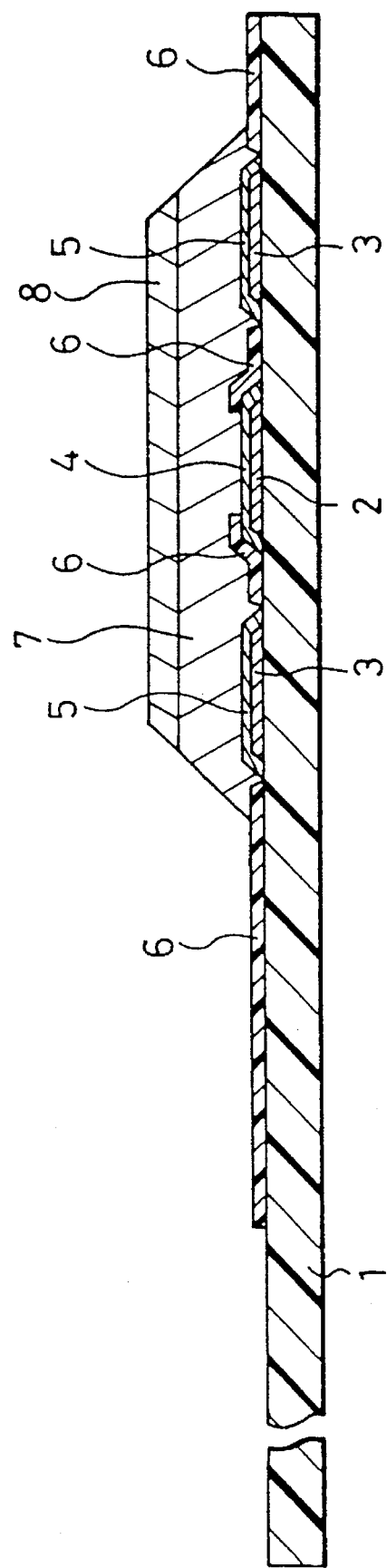
FIG. 2 is a vertical sectional view showing an essential portion of the glucose sensor.

FIG. 1 shows an exploded view of the glucose sensor, with a reaction layer omitted for clarify of viewing. An insulating base plate 1 made of polyethylene terephthalate includes leads 2 and 3 which are formed by screen printing silver pastes on one surface thereof. After forming the leads 2 and 3, a conductive carbon paste containing a resin binder is printed to form a working electrode 4o The working electrode 4 is in contact with the lead 2.

Next, an insulating paste is printed to form an insulating layer 6. The insulating layer 6 covers the periphery of the working electrode 4, thus keeping the constant area of the exposed portion of the working electrode 4. Further, the insulating layer 6 partially covers the leads 2 and 3.

Then, a conductive carbon paste containing a resin binder is printed to form a counter electrode 5 which contacts the lead 3.

An aqueous solution of carboxymethyl cellulose (hereinafter designated CMC) is dropped onto the electrode system (working electrode 4 and counter electrode 5) and is dried, to form a CMC layer. Further, an aqueous solution, which contains glucose oxidase as an enzyme and potassium ferricyanide as an electron acceptor, is dropped onto the electrode system and is dried, to form a reaction layer 7 partially mixed with the CMC layer.

Next, to ensure smoother supply of a sample solution onto the reaction layer 7, an organic solvent solution of lecithin, for example, a toluene solution, is spread from a sample supply port (at the tip of the sensor) and over the reaction layer, and is dried to form a lecithin layer 8. Finally, a cover 9 and a spacer 10 are bonded to the base plate 1, with their relative positions as defined by dashed lines in FIG. 1, to complete the fabrication of the glucose sensor.

Figure 3:
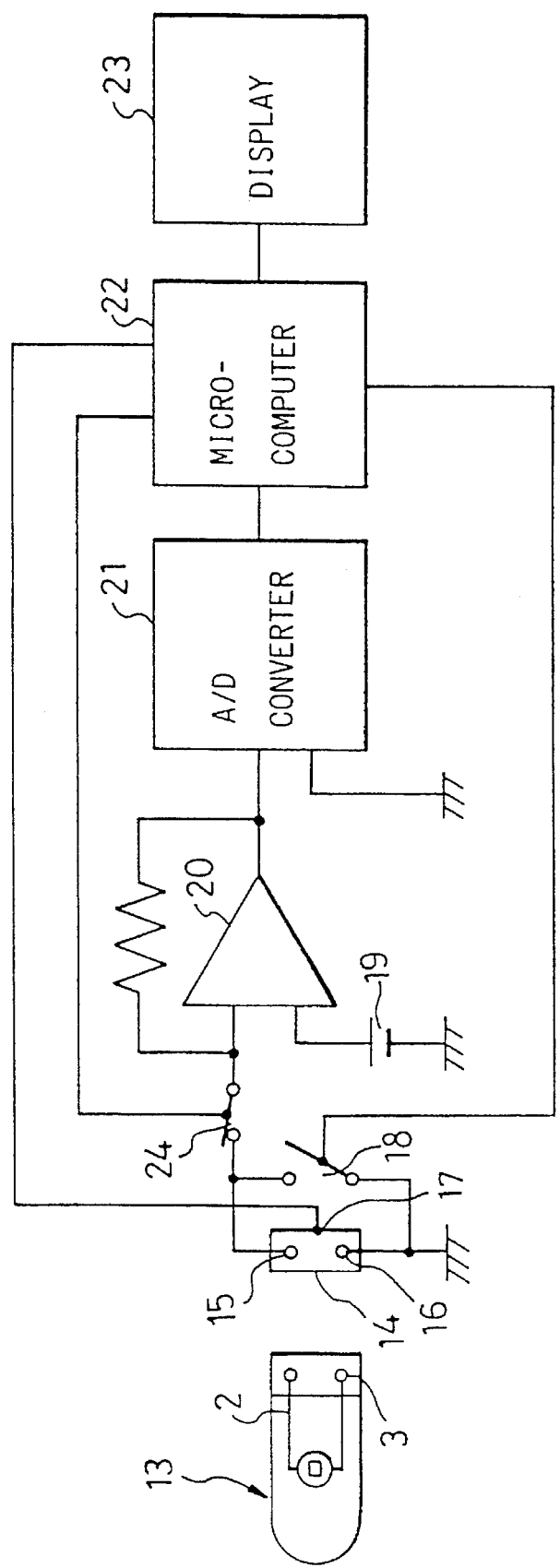
FIG. 3 is a block diagram of a measuring apparatus that uses the glucose sensor.

FIG. 3 is a block diagram of a measuring apparatus for quantifying a specific substance using the above sensor.

This apparatus will be described below.

A connector 14 has terminals 15 and 16 that are in contact with the leads 2 and 3, respectively. When the sensor 13 is inserted in the connector 14, a detection switch 17 detects the insertion of the sensor 13, and the operation hereinafter described is initiated. A switch 18, which is controlled by a microcomputer 22, is normally open as shown in the figure; when it is closed, the terminals 15 and 16 on the connector 14 are short-circuited.

Since a constant voltage is applied between the terminals 15 and 16 by a battery 19, when a sample solution is supplied to the sensor 13, a system is activated so as to detect the supply of the solution by the change in the resistance value between the working electrode 4 and the counter electrode 5. Then, the microcomputer 22 detects the change of the output voltage of a current/voltage converter 20 through an A/D converter 21, and makes a measuring timer therein to start. At the same time, the switch 18 is closed to short-circuit the working electrode 4 and counter electrode 5 of the sensor 13.

After elapsing of a predetermined time, for example, 55 seconds, the switch 18 is opened, and a predetermined voltage necessary to produce a response current is applied between the working electrode 4 and counter electrode 5 of the sensor 13. The current signal flowed between the working electrode 4 and counter electrode 5 is converted to a voltage signal by the current/voltage converter 20, and the resultant voltage value is converted into a time axis. The microcomputer 22 counts the time axis, calculates the response value, and produces the result on a display 23.

The following example explains how the circuit between the working electrode and counter electrode is alternately closed and opened.

In the above-mentioned example, a normally closed switch 24 is opened, and in that state, when the switch 18 is closed the working electrode and counter electrode are short-circuited; when the switch 18 is opened, the circuit between the working electrode and counter electrode is opened. By closing and opening the switch 18 in this manner, the circuit between the working electrode and counter electrode are alternately closed and opened.

In quantifying a specific compound, when a sample solution is introduced into the reaction layer of the sensor, if there is nonuniformity in the dissolved state of the reaction layer, a potential difference occurs between the working electrode and the counter electrode due to the nonuniform state. Then, by short-circuiting the two electrodes and thus holding them at the same potential thereby achieving a potential difference close to 0 V, the potential difference occurring between the two electrodes can be easily eliminated. Thus the above-mentioned problems can be solved.

Furthermore, by alternately closing and opening the circuit between the working electrode and the counter electrode, the electrode surfaces are electrochemically cleaned; this increases the electrode activity and improves the response characteristics.

The present invention will now be described by way of example.

EXAMPLE 1

Quantification of glucose will be described as an example of the quantifying method of the invention.

First, 3 µl of an aqueous glucose solution as a sample solution was supplied through the sample supply port 12 to the sensor of structure shown in FIG. 1. The sample solution reached the portion of an air hole 11, and dissolved the reaction layer over the electrode system.

Upon the supply of the sample solution was activated the system that detects the supply of a solution by the change in the resistance value between the counter electrode 5 and working electrode 4 of the electrode system, and the two electrodes were connected together, that is, short-circuited. After holding this state for 55 seconds, a voltage of +0.5 V was applied between the counter electrode 5 and working electrode 4 of the electrode system, and the current value five seconds thereafter was measured. The result showed a value corresponding to the glucose concentration (curve "a" shown in FIG. 4).

For comparison, after the supply of the sample solution the two electrodes were held in an open circuit state for 55 seconds, and then a voltage of +0.5 V was applied and the current value five seconds thereafter was measured. The resultant value plotted against the glucose concentration is shown by a curve "b" in FIG. 4.

Figure 4:
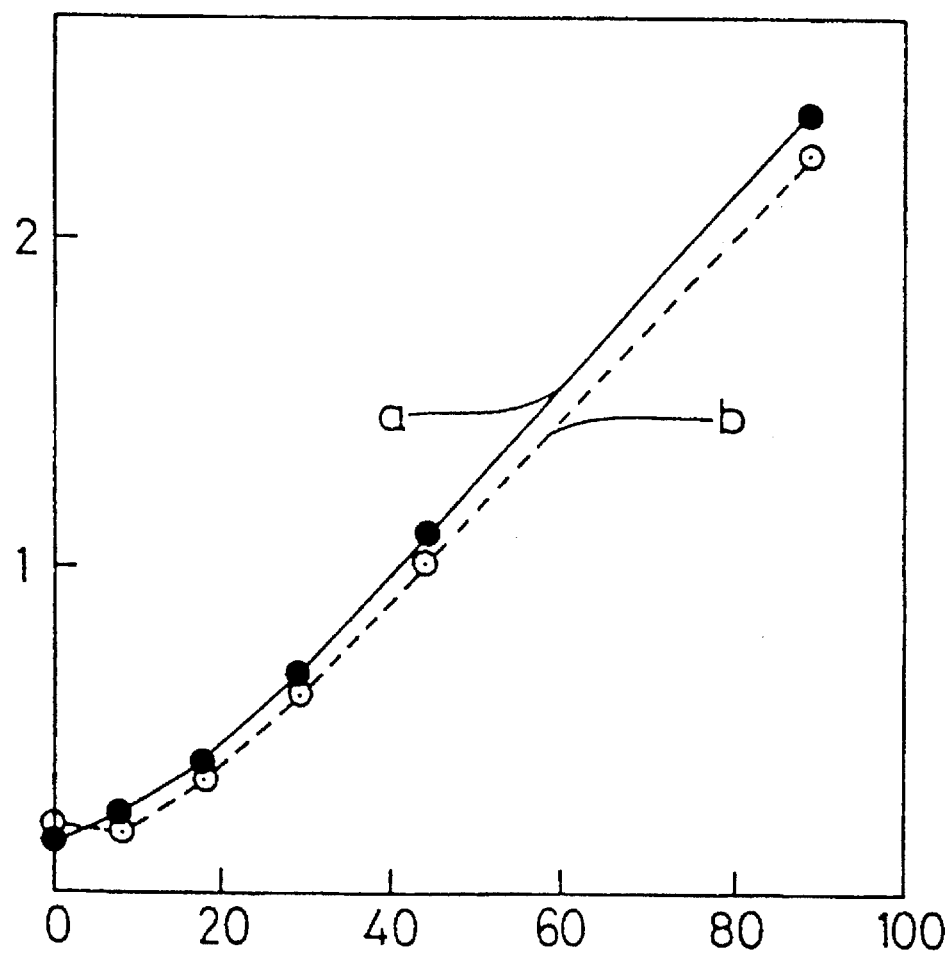
FIG. 4 is a diagram showing a response example of the glucose sensor.

When the results of the measurements, i.e., the curves "a" and "b" in FIG. 4, are compared, it can be seen that a larger current value is obtained when the voltage is applied after holding the electrodes in a short-circuit state. Furthermore, when coefficients of variation were compared, and it shows that a smaller coefficient of variation was obtained when the current value was measured after short-circuiting the two electrodes. That is, variations in the measurement result were reduced when the two electrodes were short-circuited before applying the voltage of 0.5 V. Also, the blank response (the response to the glucose concentration of 0 mg/dl) was reduced when the two electrodes were short-circuited.

EXAMPLE 2

Measurements were made using a glucose sensor of the same structure as that used in the first example.

First, 3 µl of an aqueous glucose solution as a sample solution was supplied through the sample supply port 12 to the sensor. The sample solution reached the portion of the air hole 11 and dissolved the reaction layer over the electrode system.

Figure 5:
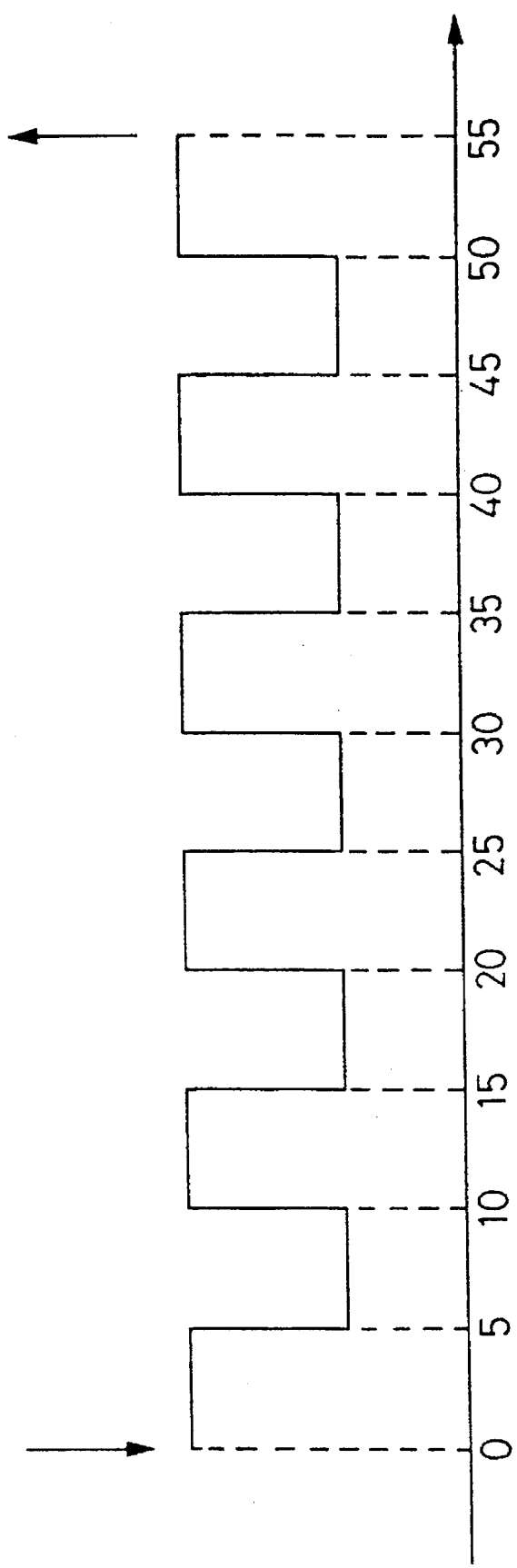
FIG. 5 is a diagram showing changes with time in the states of a short circuit and an open circuit between a working electrode and a counter electrode in one example of the present invention.

Upon the supply of the sample solution, the system that detects the supply of a solution was activated, and the two electrodes were automatically short-circuited. After being held in a short-circuit state for five seconds, the two electrodes were put in an open circuit state, and after being held in the open circuit state for five seconds, the electrodes were again short-circuited. This process was repeated five times. Finally, after holding the electrodes in a short-circuit state for five seconds, that is, 55 seconds after the supply of the sample, a voltage of +0.5 V was applied across the counter electrode 5 and the working electrode 4, and the current value five seconds thereafter was measured. The result showed a value corresponding to the glucose concentration in the sample solution. FIG. 5 shows changes with time in the states of a short circuit and an open circuit between the working electrode and the counter electrode in this example.

For comparison, after the supply of the sample solution, the electrodes were held in an open circuit state for 55 seconds, and then a voltage of +0.5 V was applied and the current value five seconds thereafter was measured.

Comparison of the results of the above-mentioned two measurements showed that better response characteristics were obtained when the voltage was applied after alternately closing and opening the circuit between the two electrodes repeatedly.

For electrodes made of platinum, gold, palladium, etc., it is known that by performing potential sweeping in an acid solution with such an electrode as a working electrode and repeating the process of hydrogen absorption and desorption and oxide film formation and dissolution on the electrode surface, the electrode surface is electrochemically cleaned and the electrode activity increases. It is believed that the repetitive alternation of short circuit and open circuit states described above produced a similar effect on the surfaces of the working electrode 4 and counter electrode 5, thus leading to improved response characteristics.

In the above-mentioned examples, the counter electrode and working electrode were short-circuited upon the supply of the sample solution, but this is not an essential condition. For example, the counter electrode and working electrode may be short-circuited before the supply of the sample solution. Further, the above-mentioned examples have dealt with a case in which the short-circuit state was maintained for 55 seconds, and a case in which the short-circuit and open circuit states were made to alternate in a repeated manner, but it will be appreciated that the invention is not limited to the illustrated cases. The short-circuit state, open circuit state, or voltage applied state may be combined in any appropriate manner before applying a voltage to obtain the response current.

Furthermore, the above examples have dealt with a method in which the reaction layer is dissolved in a sample solution, but the invention is not limited to the illustrated method. For example, the reaction layer may be made to become hardened and insoluble in a sample solution.

As has been described, according to the present invention, a reliable method of quantifying a specific compound is provided.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A method for quantifying a specific compound, which uses a biosensor comprising a reaction layer containing at least an enzyme and an electron acceptor, and an electrode system having a working electrode made of carbon and a counter electrode made of carbon formed on an insulating base plate, and which detects a change in substance concentration caused by a reaction between said enzyme and a specific compound contained in a sample by detecting an electrochemical response obtained when a voltage is applied between said working electrode and said counter electrode, wherein said electrochemical response is an oxidation current of a reduced form of said electron acceptor, and said working electrode and said counter electrode are short-circuited by closing a switch in a circuit connected to terminals of said working electrode and said counter electrode before said voltage is applied therebetween.

2. A method for quantifying a specific compound in accordance with claim 1, wherein alternation of a short circuit state and an open circuit state is repeated a plurality of times before said voltage is applied between said working electrode and said counter electrode.

3. An apparatus for quantifying a specific compound, comprising: a biosensor including a reaction layer containing at least an enzyme and an electron acceptor, and an electrode system having a working electrode made of carbon and a counter electrode made of carbon formed on an insulating base plate; means for supplying a sample solution containing a specific compound to said reaction layer of said biosensor; voltage application means for applying a predetermined voltage between said working electrode and said counter electrode of the biosensor; means for measuring an oxidation current of a reduced form of said electron acceptor flowing between said working electrode and said counter electrode to which said voltage is applied; means for short-circuiting said working electrode and said counter electrode by closing a switch in a circuit connected to terminals of said working electrode and said counter electrode before said voltage is applied between said working electrode and said counter electrode.

4. An apparatus for quantifying a specific compound in accordance with claim 3, further comprising means for alternately closing and opening a circuit between said working electrode and said counter electrode a plurality of times.

* * * * *